US012688792B2

(12) United States Patent
Fürnstahl et al.

(10) Patent No.: US 12,688,792 B2

(45) Date of Patent: Jul. 21, 2026

(54) COMPUTER IMPLEMENTED METHOD, A COMPUTING DEVICE AND A SYSTEM FOR ASSISTING BENDING OF A REINFORCING ROD FOR ATTACHMENT TO A PLURALITY OF CHIRURGICAL IMPLANTS

(71) Applicant: 25SEGMENTS AG, Zürich (CH)

(72) Inventors: Philipp Fürnstahl, Eglisau (CH);
Mazda Farshad, Zumikon (CH);
Marco Von Atzigen, Alpnach (CH)

(73) Assignee: 25SEGMENTS AG, Zurich (CH)

( * ) Notice: Subject to any disclaimer, the term of this patent is extended or adjusted under 35 U.S.C. 154(b) by 640 days.

(21) Appl. No.: 18/078,748

(22) Filed: Dec. 9, 2022

(65) Prior Publication Data

US 2023/0245589 A1      Aug. 3, 2023

(30) Foreign Application Priority Data

Feb. 2, 2022    (EP) .................................... 22154739

(51) Int. Cl.
*A61B 34/10* (2016.01)
*A61B 17/70* (2006.01)
(Continued)

(52) U.S. Cl.
CPC ........ *G09B 19/003* (2013.01); *A61B 17/7013* (2013.01); *A61B 34/10* (2016.02);
(Continued)

(58) Field of Classification Search
CPC .......... A61B 17/8863; A61B 2034/102; A61B 2034/2065; A61B 2034/252; A61B 2090/365; A61B 34/20
See application file for complete search history.

(56) References Cited

U.S. PATENT DOCUMENTS

2019/0146458 A1* 5/2019 Roh .................... G05B 19/4099
                                                                     700/98
2020/0196996 A1* 6/2020 Isaacs ................ A61B 17/7011
              (Continued)

OTHER PUBLICATIONS

Farshad, Mazda, Jose Miguel Spirig, Daniel Suter, Armando Hoch, Marco D. Burkhard, Florentin Liebmann, Nadja A. Farshad-Amacker, and Philipp Fürnstahl. "Operator independent reliability of direct augmented reality navigated pedicle screw placement and rod bending." (NASSJ) 8 (2021): 100084. (Year: 2021).*

*Primary Examiner* — Stephen R Koziol
*Assistant Examiner* — Ashley Hytrek
(74) *Attorney, Agent, or Firm* — Pauley Erickson & Swanson

(57) ABSTRACT

A computer implemented method of assisting bending of a reinforcing rod (10) includes the steps of receiving spatial positions ($P_{1-n}$) of chirurgical implants ($20_{1-n}$), in particular pedicle screws, captured by a camera-based positioning device (50), the chirurgical implants ($20_{1-n}$) configured to attach to the reinforcing rod (10); calculating a rod shape (10c) corresponding to the spatial positions ($P_{1-n}$), allowing the chirurgical implants ($201n$) to be attached to the reinforcing rod (10); based on the calculated rod shape (10c), calculating a sequence of bending parameter set(s); and generating tool operation guidance for bending tool(s) (70) based on the bending parameter set(s), the tool operation guidance indicating a sequence of prescribed operation steps ($S_{1-n}$), wherein the sequence of prescribed operation steps ($S_{1-n}$) are determined such, that when carried out using the bending tool(s) (70), causes the bending tool(s) (70) to shape the reinforcing rod (10) corresponding to the calculated rod shape (10c).

16 Claims, 8 Drawing Sheets

(51) Int. Cl.

| | | |
|---|---|---|
| *G02B 27/01* | (2006.01) | |
| *G06T 7/70* | (2017.01) | |
| *G06T 19/00* | (2011.01) | |
| *G09B 19/00* | (2006.01) | |
| *G09B 19/24* | (2006.01) | |
| *H04N 13/239* | (2018.01) | |
| *H04N 13/296* | (2018.01) | |

(52) U.S. Cl.

CPC ................ *G06T 7/70* (2017.01); *G06T 19/00* (2013.01); *G09B 19/24* (2013.01); *A61B 2034/108* (2016.02); *G02B 27/017* (2013.01); *G06T 2207/10012* (2013.01); *G06T 2207/20081* (2013.01); *G06T 2207/20084* (2013.01); *G06T 2207/30052* (2013.01); *H04N 13/239* (2018.05); *H04N 13/296* (2018.05)

(56) References Cited

U.S. PATENT DOCUMENTS

| | | | |
|---|---|---|---|
| 2020/0197107 A1* | 6/2020 | Ryan ...................... | A61B 34/20 |
| 2021/0169578 A1* | 6/2021 | Calloway ........... | G02B 27/0172 |
| 2021/0169605 A1* | 6/2021 | Calloway ............... | A61B 34/10 |
| 2021/0330388 A1* | 10/2021 | Den Hartog ........... | A61B 34/10 |
| 2024/0058064 A1* | 2/2024 | Weiser ................... | A61B 34/10 |
| 2024/0390050 A1* | 11/2024 | Mariampillai ..... | A61B 17/8863 |

* cited by examiner

Figure 2:
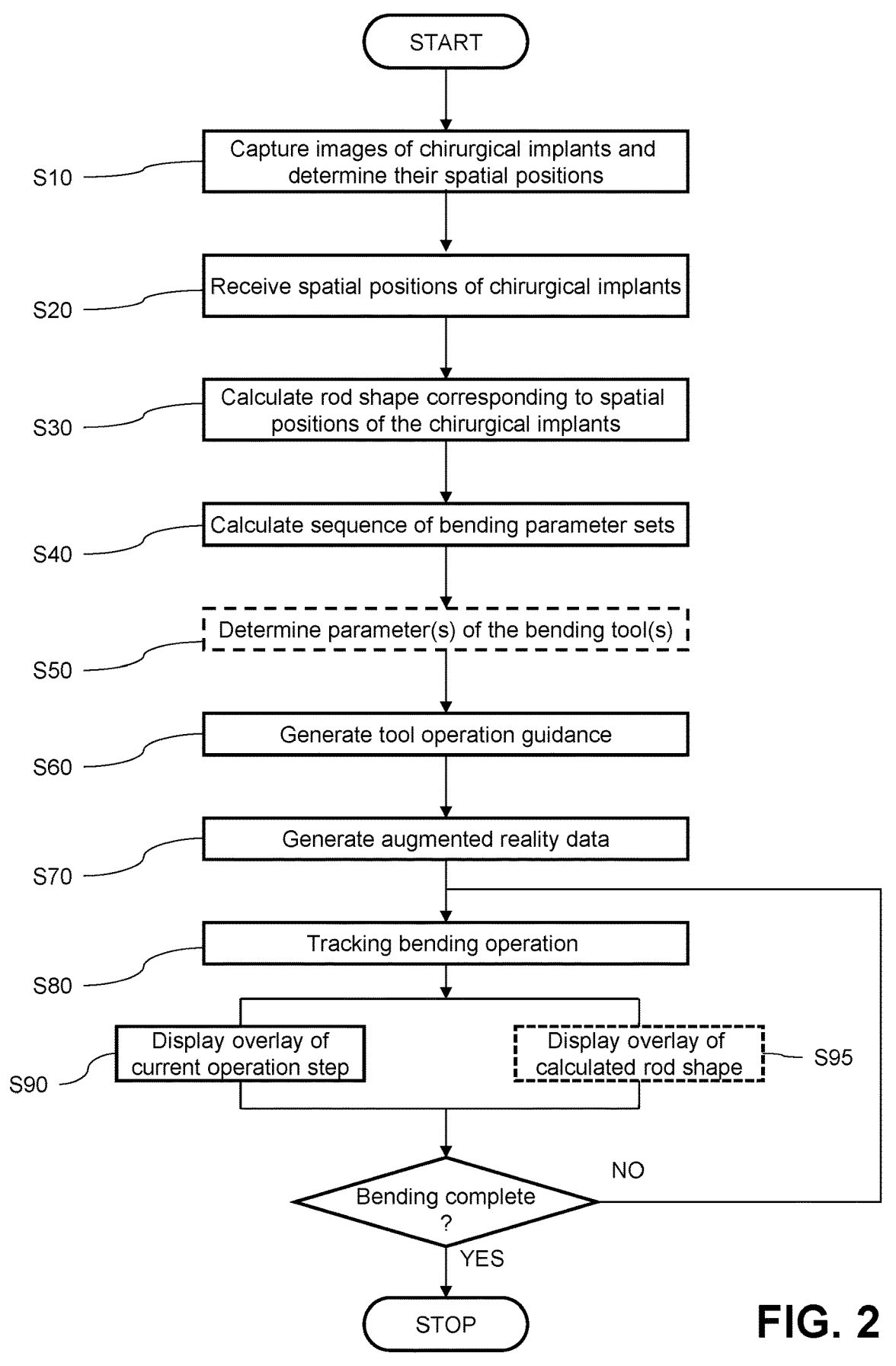

START

S10 — Capture images of chirurgical implants and determine their spatial positions S20 — Receive spatial positions of chirurgical implants S30 — Calculate rod shape corresponding to spatial positions of the chirurgical implants S40 — Calculate sequence of bending parameter sets S50 — Determine parameter(s) of the bending tool(s)

S60 — Generate tool operation guidance

S70 — Generate augmented reality data

S80 — Tracking bending operation

S90 — Display overlay of current operation step

Display overlay of calculated rod shape — S95

Bending complete ? — NO

YES

STOP

S12 — Capture stream of stereographic images of the chirurgical implants

S14 — Process stream of stereographic images to determine spatial positions of the chirurgical implants using stereo neuronal network Position determination complete?

NO

YES

Capture images of chirurgical implants and determine their spatial positions

Stereo Neural Network union bounding box $_L\Delta w_i$    $_R\Delta w_i$

22 from right camera    $_R\Delta x_i$  $_L\Delta x_i$    from left camera $cx_i$ $cy_i$ $aw$ $bw_i$ $ah$  $bh_i$    $\sigma(ty_i)$ $\sigma(tx_i)$ $bx_i = \sigma(tx_i) + cx_i$
$by_i = \sigma(ty_i) + cy_i$
$bw_i = awe^{tw_i}$
$bh_i = ahe^{th_i}$

COMPUTER IMPLEMENTED METHOD, A COMPUTING DEVICE AND A SYSTEM FOR ASSISTING BENDING OF A REINFORCING ROD FOR ATTACHMENT TO A PLURALITY OF CHIRURGICAL IMPLANTS

CROSS-REFERENCE TO RELATED APPLICATIONS

European Patent Application No. 22154739.1, filed 2 Feb. 2022, the priority document corresponding to this invention, to which a foreign priority benefit is claimed under Title 35, United States Code, Section 119, and their entire teachings are incorporated, by reference, into this specification.

BACKGROUND OF THE INVENTION

Field of the Invention

The present invention relates to a computer implemented method, a computing device, a system and a computer program product for assisting bending of a reinforcing rod for attachment to a plurality of chirurgical implants, in particular pedicle screws.

Discussion of Related Art

Spinal fusion surgery is indicated for a variety of spinal disorders including deformity, trauma, degenerative disc disease, scoliosis, and spondylolisthesis. In the course of the surgery, pedicle screw implants are bilaterally inserted into the pedicles of pathological vertebrae and fused using a reinforcing rod to form a rigid connection. With a complication rate of up to 15%, the surgical treatment of the spine remains very challenging because the surgeon has to operate close to vital anatomical structures such as the spinal cord, nerve roots, and arteries. Due to the high risk of injury, spine surgery was one of the first surgical disciplines leveraging surgical navigation to enable more accurate and safer surgical execution. Pedicle screw placement is a frequently navigated surgical step in spinal surgery, whereas navigation of the rod bending process remains an almost unexplored field. Conventionally, computer assisted navigation of pedicle screw placement relies on externally tracked markers in combination with medical imaging techniques such as Computed Tomography (CT) or fluoroscopy to match a preoperatively generated intervention plan to the intraoperative anatomy. After a successful registration, the plan can be navigated by providing computer assistance as desired screw entry points and drilling trajectories to the surgeon.

After the chirurgical implants, in particular pedicle screws, have been implanted into the vertebrae, a reinforcing rod has to be adapted to the patient's anatomy so that it can be attached to the pedicle screws, in particular such as to fit into U-shaped openings of the pedicle screw heads. A surgical bending tool, in particular a bending bench is commonly used to bend the reinforcing rod pre- or intra-operatively. For each bending attempt, the axial rod position in the bending bench needs to be adjusted to guarantee bending in the desired location. In addition, the reinforcing rod must be rotated axially during bending to allow 3D bends since the bending bench always applies the bending force in a constant direction. Eventually, the bending is executed by pressing down a lever of the bending bench.

In conventional clinical practice, surgeons choose each of the aforementioned parameters by visual judgment and execute the bending based on their experience. Each reinforcing rod requires several bending steps until its final shape is reached. In the course of the bending process, surgeons have to move back and forth between the bending bench and the anatomy (patient) to iteratively refine the shape of the reinforcing rod. Reinforcing rod shape adaptations after initiation of the implantation process are denoted rebending maneuvers and are associated with inferior initial reinforcing rod quality and prolonged surgery time. A reduction of the number of rebending attempts is therefore a clinical requirement and a surgical goal. The procedure is finished when the reinforcing rod fits smoothly into the U-shaped pedicle screw heads. Misalignment of the reinforcing rod with respect to the pedicle screw heads results in a forceful reduction of the reinforcing rod which can, in turn, lead to screw loosening or even pull-out of the pedicle screw(s).

The combination of potential reinforcing rod misalignment and time-consuming efforts and potentially compromised sterility arising from moving back and forth between bending bench and anatomy promotes the use of computer assistance of the bending procedure.

So far only a few approaches to computer assistance of bending of spinal reinforcing rods have been proposed. One of the few known approaches initially requires the surgeons to capture the locations of the implanted pedicle screws (respectively fixation points thereof) using an optically tracked pointing device. The pointing device is conventionally tracked using a stationary tracking device which needs to be precisely calibrated before surgery. The obtained spatial locations of the pedicle screws, in particular their fixation points are then translated into a computer model of the desired reinforcing rod shape. In the next step, the target rod shape is converted into a set of bending positions and bending angles which are provided to the surgeons for execution with a proprietary bending tool. While the proposed approach does have the potential to streamline the shaping of reinforcing rods, the additional preparation and maintenance effort, the proprietary surgical tools, and the expensive hardware such as an external tracking system that needs to be installed and calibrated in the operating room for each intervention pose limitations to this solution's adaptation.

SUMMARY OF THE INVENTION

It is an object of the present invention to provide a method, computing device, a system and a computer program product for assisting bending of a reinforcing rod to the specific anatomy of a patient that overcomes one or more of the disadvantages of the prior art. In particular, it is an object of the present invention to provide an alternative method, computing device, a system and a computer program product, of assisting bending of a reinforcing rod that allows precise shaping of a reinforcing rod to the spatial positions of a plurality of chirurgical implants attached to a patient, minimizing rebending attempts, hence reducing surgery time—which is compatible with conventional bending tools and thus eliminating the need for specialized, proprietary bending tool(s).

According to the present disclosure, this object is addressed by the features of the independent claims. In addition, further advantageous embodiments follow from the dependent claims and the description.

In particular, this object is achieved by a computer implemented method of assisting bending of a reinforcing rod, the method comprising the steps carried out by a computing device: receiving spatial positions of a plurality of chirurgical implants; calculating a rod shape corresponding to the spatial positions of the plurality of chirurgical implants; calculating bending parameter set(s); and generating tool operation guidance for bending tool(s) based on the bending parameter set(s).

Each of the chirurgical implants, in particular pedicle screws, is configured to be attachable to the reinforcing rod, for example by means of openings in the chirurgical implants, called tulips, the openings having a dimension selected such as to be able to receive a section of the reinforcing rod to guarantee a strong rigid postoperative connection.

The spatial positions of a plurality of chirurgical implants, in particular pedicle screws, received by the computing device are captured by a camera-based positioning device.

The step of calculating a rod shape corresponding to the spatial positions of the plurality of chirurgical implants, comprises calculating a rod shape that allows the reinforcing rod to be attached to the plurality of chirurgical implants.

The bending parameter set(s) calculated based on the calculated rod shape define a series of parameters descriptive of a reinforcing rod having the calculated rod shape. In particular, the bending parameters comprise one or more of: a series of rod distances between consecutive bends of the reinforcing rod, a series of axial reorientation angles indicative of an angle by which the reinforcing rod needs to be rotated around its longitudinal axis between consecutive bends; and a rod bending angle indicative of an angle of a respective bend of the reinforcing rod—in a radial direction with respect to the reinforcing rod. According to embodiments, the bending parameter set(s) further comprise bending radii, indicative of the radius of the bends of the reinforcing rod.

The tool operation guidance, generated for specific bending tool(s) based on the bending parameter set(s), indicates a sequence of prescribed operation steps of the bending tool(s). For example, the bending tools comprise a bending bench for applying a bending force onto a section of the reinforcing rod and a retaining tool for holding the reinforcing rod during bending and/or for rotating the reinforcing rod around its longitudinal axis.

The sequence of prescribed operation steps $S_{1-n}$ are determined such, that when the steps are carried out, e.g. by a surgeon, using the specific bending tool(s), causes the bending tool(s) to shape the reinforcing rod from an initial form into a shaped form corresponding to the calculated rod shape. Commonly, the initial form is a straight rod section while the shaped form is essentially identical to the calculated rod shape, within a defined tolerance. In other words, while the calculated rod shape describes how the desired final shape of the reinforcing rod, the tool operation guidance describes how this desired rod shape can be achieved using the specific bending tool(s).

In particular, the tool operation guidance is generated based on one or more of the following: parameter(s) of the bending tool(s); parameter(s) of the reinforcing rod; and/or the positions of fixation points of the plurality of chirurgical implants. Parameter(s) of the bending tool(s) comprise one or more of: a bending radius (fixed or adjustable), data descriptive of the geometry of a bending lever, data descriptive of the geometry of a restraining element for receiving the reinforcing rod. The parameter(s) of the reinforcing rod comprise one or more of: initial form (e.g., straight rod section), physical dimension(s) (e.g.; length, diameter), material properties (e.g., modulus of elasticity, stiffness).

According to particular embodiments disclosed herein, the method further comprises generating augmented reality data based on the tool operation guidance. The augmented reality data comprises a sequence of overlays representing the prescribed operation steps of the tool operation guidance. A display device of the camera-based positioning device is controlled by the computing device such that the overlays are sequentially superimposed on a user's view of the bending tool(s).

According to embodiments wherein the display device is a see-through display device (e.g. of a head-mounted augmented reality headset), wherein the user views the bending tool(s) through the display device, the overlay is generated as a 3D overlay and the camera-based positioning device is controlled by the computing device such that the overlay is projected in the field of view of the user, through the see-through display device, at a corresponding position with respect to the bending tool(s).

According to particular embodiments, the overlay represents a specific operation step as a visualization of the bending tool(s) in an actuated position (e.g., rotational or translator displacement of a lever arm) which causes the reinforcing rod to be bent according to the corresponding bending parameter set.

In order to provide a seamless operating experience, according to embodiments disclosed herein, the method further comprises tracking a progress of the sequence of prescribed operation steps and displaying the overlay representing a particular operation step according to the tracking. The tracking of the progress of the shaping process, i.e., the execution of the sequence of prescribed operation steps of the bending tool(s) is performed using the camera-based positioning device, for example by repeatedly capturing the shape of the reinforcing rod and comparing it with the calculated rod shape. Based on this tracking, an overlay of the current or the next operation step of the sequence of prescribed operation steps is displayed on the display device to aid the user in carrying out the current/next bending step according to the corresponding prescribed operation step.

To further improve the user experience, respectively to allow the user to verify the progress of the sequence of prescribed operation steps and/or to verify the current shape of the reinforcing rod, according to embodiments disclosed herein, the method further comprises generating augmented reality data based on the calculated rod shape. The augmented reality data generated based on the calculated rod shape comprises an overlay representing the calculated rod shape. The camera-based positioning device is further controlled by the computing device to display the overlay representing the calculated rod shape on the display device such that the overlay is superimposed on a user's view of the reinforcing rod. According to embodiments wherein the display device is a see-through display device (e.g., of a head-mounted augmented reality headset), wherein the user views the reinforcing rod through the display device, the camera-based positioning device is controlled by the computing device such that overlay representing the calculated rod shape is projected in the field of view of the user, through the see-through display device, at a corresponding position with respect to the reinforcing rod.

It is an object of further embodiments disclosed herein to provide an alternative method, computing device, system and computer program product, of assisting bending of a reinforcing rod that allows precise shaping of a reinforcing rod to the spatial positions of a plurality of chirurgical implants attached to a patient, which does not require a surgeon to manually identify the chirurgical implants and does not require two or more separate devices for bending guidance and for detecting the positions of the chirurgical implants.

This further object is addressed by embodiments disclosed herein in that the method further comprises controlling, by the computing device, the camera-based positioning device to capture image(s) of the plurality of chirurgical implants and determining the spatial positions of the plurality of chirurgical implants based on the captured images. In other words, the same device (the camera-based positioning device) is controlled both for determining the spatial positions of the chirurgical implants as well as for displaying the tool operation guidance.

According to embodiments disclosed herein, the computing device controls the camera-based positioning device to capture stereo images of the plurality of chirurgical implants, the stereo images comprising a pair of images capturing the respective chirurgical implant from two points of view, e.g., using a pair of left and right image capture sensors arranged at a predetermined spacing apart from each other. The spatial positions of the plurality of chirurgical implants are then determined by processing the stereo images, in view of the two points of view, e.g., in view of the spacing between the pair of image capture sensors.

In order to improve precision of determining the spatial positions of the plurality of chirurgical implants, according to embodiments disclosed herein, the camera-based positioning device is controlled to capture a stream of stereo images of the plurality of chirurgical implants, the determined spatial positions of the plurality of chirurgical implants being iteratively refined by processing the stream of stereo images.

According to particular embodiments, the computing device determines the spatial positions of the plurality of chirurgical implants by processing the stereo images using a stereo neural network, the neural network having been trained with a dataset of stereo images of chirurgical implants and corresponding annotations indicative of spatial positions of chirurgical implants (other than the chirurgical implants of the current procedure).

It is an object of further embodiments disclosed herein to provide an alternative method, computing device, system and computer program product, of assisting bending of a reinforcing rod that allows precise shaping of a reinforcing rod to the spatial positions of a plurality of chirurgical implants attached to a patient, which is able to adapt to different bending tool(s) used in a surgery, without the parameter(s) of the bending tool(s) having to be manually input/selected during the surgery. This object is address in that, the camera-based positioning device is further controlled to capture image(s) of the bending tool(s) and parameter(s) of the bending tool(s) are retrieved (e.g., from a database) based on identifying the bending tools(s) using the captured images. Alternatively, or additionally, parameter(s) of the bending tool(s) are determined using the captured images (e.g., by estimating the geometry of the bending tool(s) and calculating the corresponding properties).

The above-identified objects are further achieved by a computing device comprising a processing unit and a memory unit. The memory unit comprises instructions, which, when executed by the processing unit cause the computing device to carry out the method of assisting bending of a reinforcing rod according to one of the embodiments disclosed herein. According to embodiments, the computing device is a stand-alone computer communicatively connected to the camera-based positioning device. Alternatively, or additionally, the computing device is a remote computer (e.g., a cloud-based computer) communicatively connected to the camera-based positioning device using a communication network, in particular at least partially using a mobile communication network. Alternatively, or additionally, the computing device is integrated into the camera-based positioning device.

The above-identified objects are further achieved by a system for assisting bending of a reinforcing rod, the system comprising a computing device and a camera-based positioning device communicatively connected to the computing device, the computing device comprising a processing unit and a memory unit comprising instructions, which, when executed by the processing unit cause the computing device to carry out the method of assisting bending of a reinforcing rod according to one of the embodiments disclosed herein. The camera-based positioning device comprises two or more image capture sensors and a display device (e.g., a translucent see-through display device) for displaying overlays of the tool operation guidance, and depending on embodiment, the calculated rod shape. In particular, the camera-based positioning device is a head-mounted augmented reality device.

The above-identified objects are further achieved by a computer program product, comprising instructions, which, when carried out by a processing unit of a computing device, cause the computing device to carry out the method of assisting bending of a reinforcing rod according to any one of the embodiments disclosed herein.

In summary, embodiments of the present invention address the aforementioned drawbacks of the prior art by combining a purely vision-based method for estimating the spatial positions of chirurgical implants with novel augmented reality-based step-by-step instructions to achieve bending assistance.

It is to be understood that both the foregoing general description and the following detailed description present embodiments, and are intended to provide an overview or framework for understanding the nature and character of the disclosure. The accompanying drawings are included to provide a further understanding, and are incorporated into and constitute a part of this specification. The drawings illustrate various embodiments, and together with the description serve to explain the principles and operation of the concepts disclosed.

BRIEF DESCRIPTION OF SEVERAL VIEWS OF THE DRAWINGS

The herein described invention will be more fully understood from the detailed description given herein below and the accompanying drawings which should not be considered limiting to the invention described in the appended claims. The drawings are showing:

FIG. 2 shows a flowchart illustrating steps of a further embodiment of the computer implemented method of assisting bending of a reinforcing rod, according to the present disclosure, comprising tracking of the bending operation;

DESCRIPTION OF PREFERRED EMBODIMENTS

Reference will now be made in detail to certain embodiments, examples of which are illustrated in the accompanying drawings, in which some, but not all features are shown. Indeed, embodiments disclosed herein may be embodied in many different forms and should not be construed as limited to the embodiments set forth herein; rather, these embodiments are provided so that this disclosure will satisfy applicable legal requirements. Whenever possible, like reference numbers will be used to refer to like components or parts.

Figure 1:
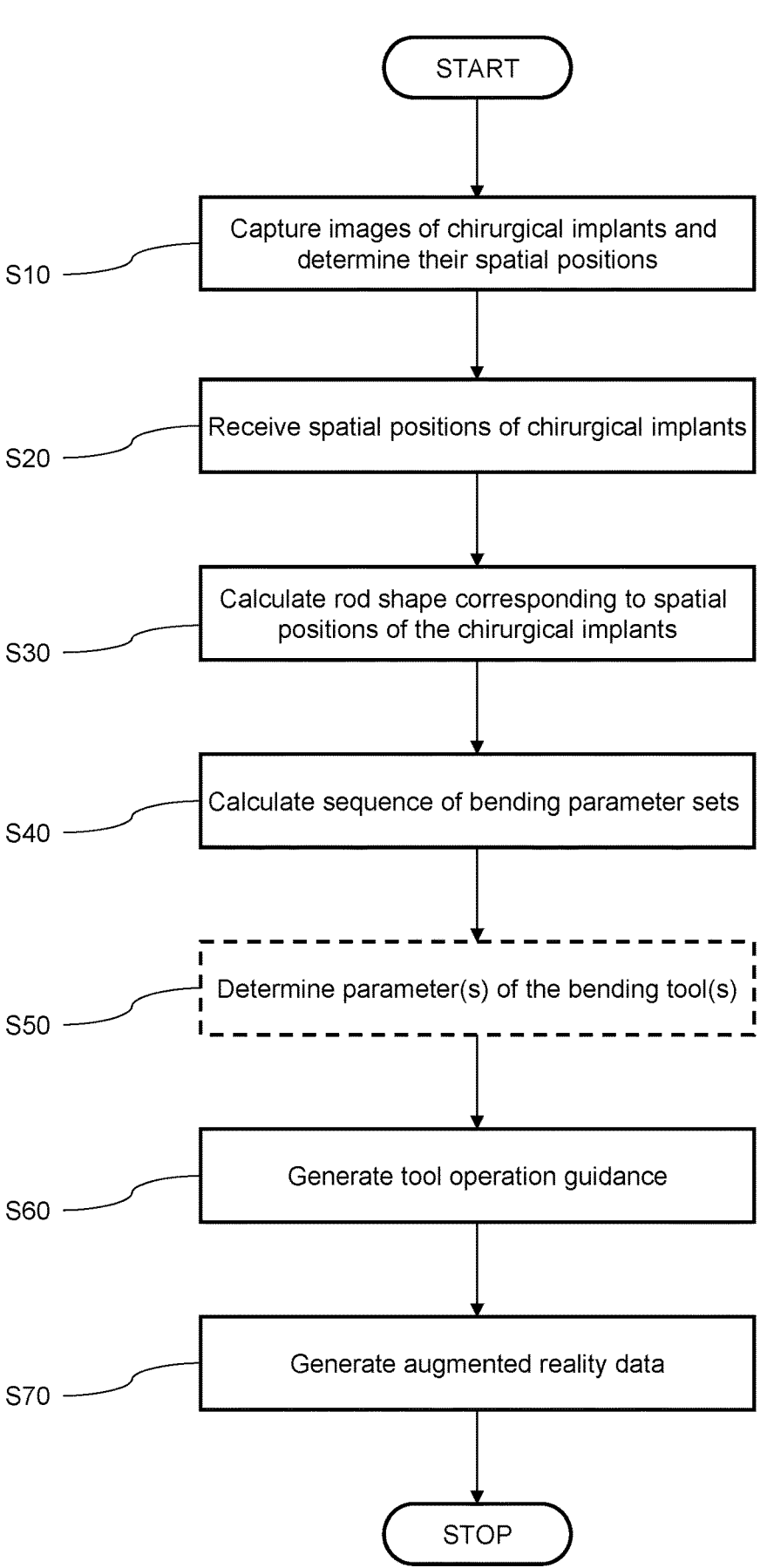
FIG. 1 shows a flowchart illustrating steps of an embodiment of the computer implemented method of assisting bending of a reinforcing rod, according to the present disclosure.

FIG. 1 shows a flowchart illustrating steps of an embodiment of the computer implemented method of assisting bending of a reinforcing rod 10 attachable to a plurality of chirurgical implants $20_{1-n}$. In step S10, a stream of stereo images, each capturing one or more of the chirurgical implants $20_{1-n}$, are streamed from a head-mounted camera-based positioning device 50 comprising two spaced apart image capture sensors 54L, 54R. Thereafter, the spatial positions $P_{1-n}$ of the plurality of chirurgical implants $20_{1-n}$ are determined in three-dimensional space using a positioning algorithm, described in detail with reference to the FIGS. 11, 12A and 12B, based on the stereo images. In a particular embodiment, the determined spatial positions $P_{1-n}$ of the plurality of chirurgical implants $20_{1-n}$ is iteratively refined using the sequence of stereo images.

In step S20, the spatial positions $P_{1-n}$ of the chirurgical implants $20_{1-n}$ are received by the computing device 100. According to embodiments, the computing device 100 itself determines the spatial positions $P_{1-n}$, in which case the term "receive" relates to data generated, transmitted and received within the computing device 100, in particular within logical, functional or structural modules thereof (e.g., image processing module, position determination module, rod shape calculation module).

In subsequent step S30, a calculated rod shape 10c is determined corresponding to the spatial positions $P_{1-n}$ of the plurality of chirurgical implants $20_{1-n}$, such as to allow the plurality of chirurgical implants $20_{1-n}$ to be attached to the rein-forcing rod 10. In particular, the calculated rod shape 10c is determined such as to allow fixation points 22 (tulips) at the end of the chirurgical implants $20_{1-n}$ to receive corresponding sections of the reinforcing rod 10. Due to the very tight fit between the fixation points 22 and the reinforcing rod 10, the calculated rod shape 10c is determined such that the reinforcing rod 10 comprises straight sections where the reinforcing rod 10 is to be attached to the fixation points 22 of the chirurgical implants $20_{1-n}$. Determination of the calculated rod shape 10c is described in detail with reference to FIGS. 11, 12A and 12B.

Having determined the calculated rod shape 10c, in step S40, a sequence of bending parameter set(s) is calculated based on the calculated rod shape 10c. The sequence of bending parameter set(s) defines a series of parameters descriptive of a reinforcing rod 10 having the calculated rod shape 10c. In particular, the sequence of bending parameter set(s) describes a sequence of sections (rod section distance $dARP_{1-n}$) of the reinforcing rod 10 as well as bends between subsequent sections, each bend being described by an axial reorientation angle $\alpha_{1-n}$ and a rod bending angle $\beta_{1-n}$ and optionally by a bending radius $R_{1-n}$, see FIG. 7A.

According to particular embodiments, shown of FIG. 1 with dashed lines, in a step S50, parameter(s) of the bending tool(s) 70 is/are determined. In a first substep of step S50, the camera-based positioning device 50 is controlled to capture image(s) of the bending tool(s) 70. Thereafter, the bending tools(s) 70 are identified using the captured images (e.g., by means of an identifier tag associated with each bending tool) and parameter(s) of the bending tool(s) 70 are retrieved (e.g., from a database stored within or communicatively connected to the computing device 100) based on the identification.

In a subsequent step S60, tool operation guidance is generated specific to the bending tools 70 based on the bending parameter sets and, depending on embodiment, further based on parameter(s) of the bending tool(s) 70. The tool operation guidance indicates a sequence of prescribed operation steps $S_{1-n}$ of the bending tool(s) 70. In the embodiments described in detail and illustrated in the figures, the bending tools comprise a bending bench 70 for applying a bending force onto a section of the reinforcing rod 10 and a retaining tool for holding the reinforcing rod 10 during bending. Correspondingly, each of the sequence of prescribed operation steps $S_{1-n}$ comprises an indication on how to operate the bending bench 70 and the retaining tool such as to shape the rein-forcing rod 10 from an initial shape 10i to a shaped form 10s corresponding to the calculated rod shape 10c. For example, each of the sequence of prescribed operation steps $S_{1-n}$ indicates a rod section distance $dARP_{1-n}$, an axial rod rotation $\alpha_{1-n}$ to be applied using the retaining tool and a lever angle (of bending tool 70) $\theta_{1-n}$ for displacing the bending bench 70 from a resting (or neutral) position thereof. When a user, in particular a surgeon, applies the sequence of prescribed operation steps $S_{1-n}$ using the retaining tool and the bending bench 70, by sequentially displacing the reinforcing rod 10 by distances $dARP_{1-n}$, rotating the reinforcing rod 10 around its longitudinal axis by axial reorientation angles $\alpha_{1-n}$ and displacing a lever arm 71 of the bending bench 70 by a lever angle (of bending tool 70) $\theta_{1-n}$, step-by-step the reinforcing rod 10 will be shaped from an initial form 10$i$ into a shaped form 10$s$ matching the calculated rod shape 10$c$, except for a defined tolerance.

Having generated the tool operation guidance, in a subsequent step S70, augmented reality data is generated based on the tool operation guidance. The augmented reality data comprises a sequence of overlays, each overlay representing a prescribed operation step S in of the tool operation guidance $OG_{1-n}$.

The assisted bending process is performed (by a user) as follows:

In a preparatory step, an overlay $OG_1$ of a retaining tool to control axial rotation os the reinforcing rod 10 is displayed. The displayed retaining tool is for example a rod gripper instrument (such as a forceps) specifically designed for holding reinforcing rods 10 without any slippage. The surgeon fixes the real-world retaining tool to the end of the reinforcing rod 10 and aligns the position and orientation of the retaining tool with the augmented-reality overlays $OG_{1-n}$.

For a $k_{th}$ bending step:

Axial reorientation: the axial orientation $\alpha_k$ of the reinforcing rod is accomplished by aligning the retaining tool axially to the presented overlay $OG_k$. Axial displacement: To guarantee the bending of the reinforcing rod 10 at the correct position, the reinforcing rod 10 is shifted axially by dARPk. This step is navigated using the same overlay $OG_k$ of the retaining tool as for the axial reorientation. Again, the actual retaining tool that are rigidly connected to the reinforcing rod 10 need to coincide with the presented overlay $OG_k$.

Lever movement: The navigation of the bending is achieved by showing the start and end positions of the lever 71 of the bending bench 70, as illustrated in light and dark gray in FIG. 7A, respectively. While the start position is fixed, the end position of the lever 71 is displayed according to $OG_k$.

Inspection: An overlay of the calculated rod shape 10$c$ is presented to the surgeon, superimposed on a view of the current shape of the reinforcing rod 10$c$, as illustrated in dark and light grey in FIG. 7B, respectively. The current shape of the reinforcing rod 10$c$ can be verified by visual inspection and adjustments can be made if necessary.

FIG. 2 shows a flowchart of a particular embodiment, wherein, in step S80, the progress of the sequence of prescribed operation steps $S_{1-n}$ of the bending tool(s) 70 is tracked using the camera-based positioning device 50.

Tracking of the progress of the sequence of prescribed operation steps $S_{1-n}$ is performed by processing a stream of stereo images from the camera-based positioning device 50 in order to identify a current shape of the reinforcing rod 10 and comparing the current shape 10$t$ of the reinforcing rod 10 with the calculated rod shape 10$c$. Based on the comparison, the progress of the execution of the prescribed operation steps $S_{1-n}$ can be determined, e.g., as the last executed step. Alternatively, or additionally, the tracking of the progress of the sequence of prescribed operation steps $S_{1-n}$ in is performed by processing a stream of stereo images from the camera-based positioning device 50 in order to identify the current/latest of the prescribed operation steps $S_{1-n}$ carried out by the surgeon using the bending tools 70.

In a subsequent step S90, as long as the bending is not completed (based on the tracking of the progress), a display device 52 of the camera-based positioning device 50 is controlled by the computing device 100 such as to superimpose the current overlay $OG_{1-n}$ in accordance with the determined progress (e.g., the first prescribed operation step $S_{1-n}$ not yet completed) onto a user's view of the bending tool(s) 70.

Figure 7A:
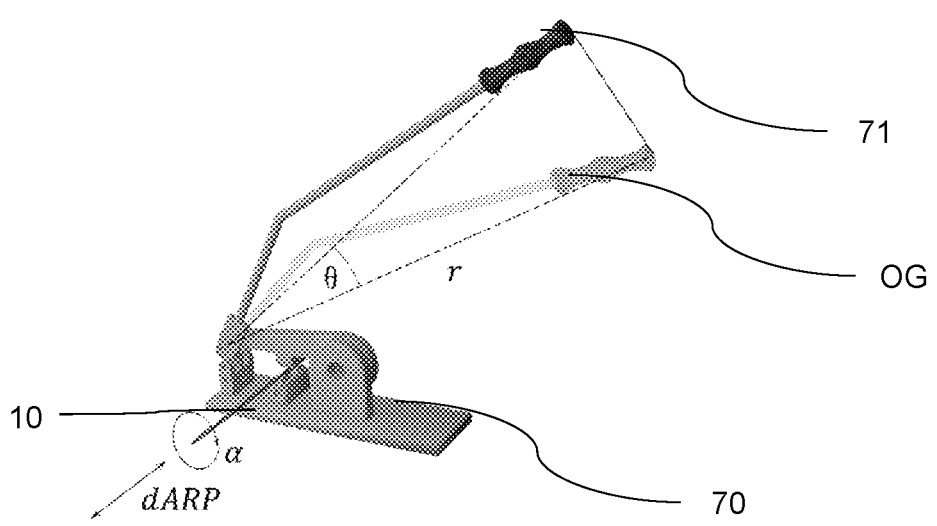
FIG. 7A shows a schematic perspective view of a bending tool receiving a reinforcing rod, illustrating parameters of a bending parameter set and an overlay of the representing the tool operation guidance.
Figure 7B:
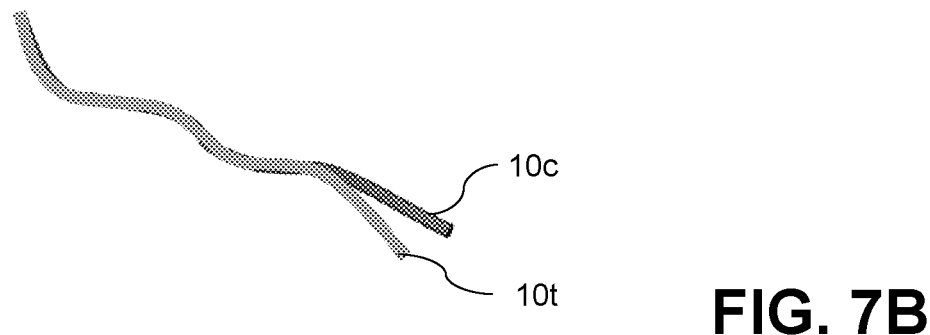
FIG. 7B shows a schematic perspective view of an overlay of a calculated rod shape superimposed on a user's view of the reinforcing rod in its current shape.

According to embodiments, in addition to displaying an overlay $OG_{1-n}$ of the current operation step of the tool operation guidance, as long as the bending is not completed (based on the tracking of the progress), in a step S95 an overlay representing the calculated rod shape $O10c$ is superimposed on a user's view of the reinforcing rod 10 through the display device 52, as illustrated on FIG. 7B. This enables the user to visually compare the current shape 10$t$ of the reinforcing rod 10 with the calculated rod shape 10$c$.

Figure 3:
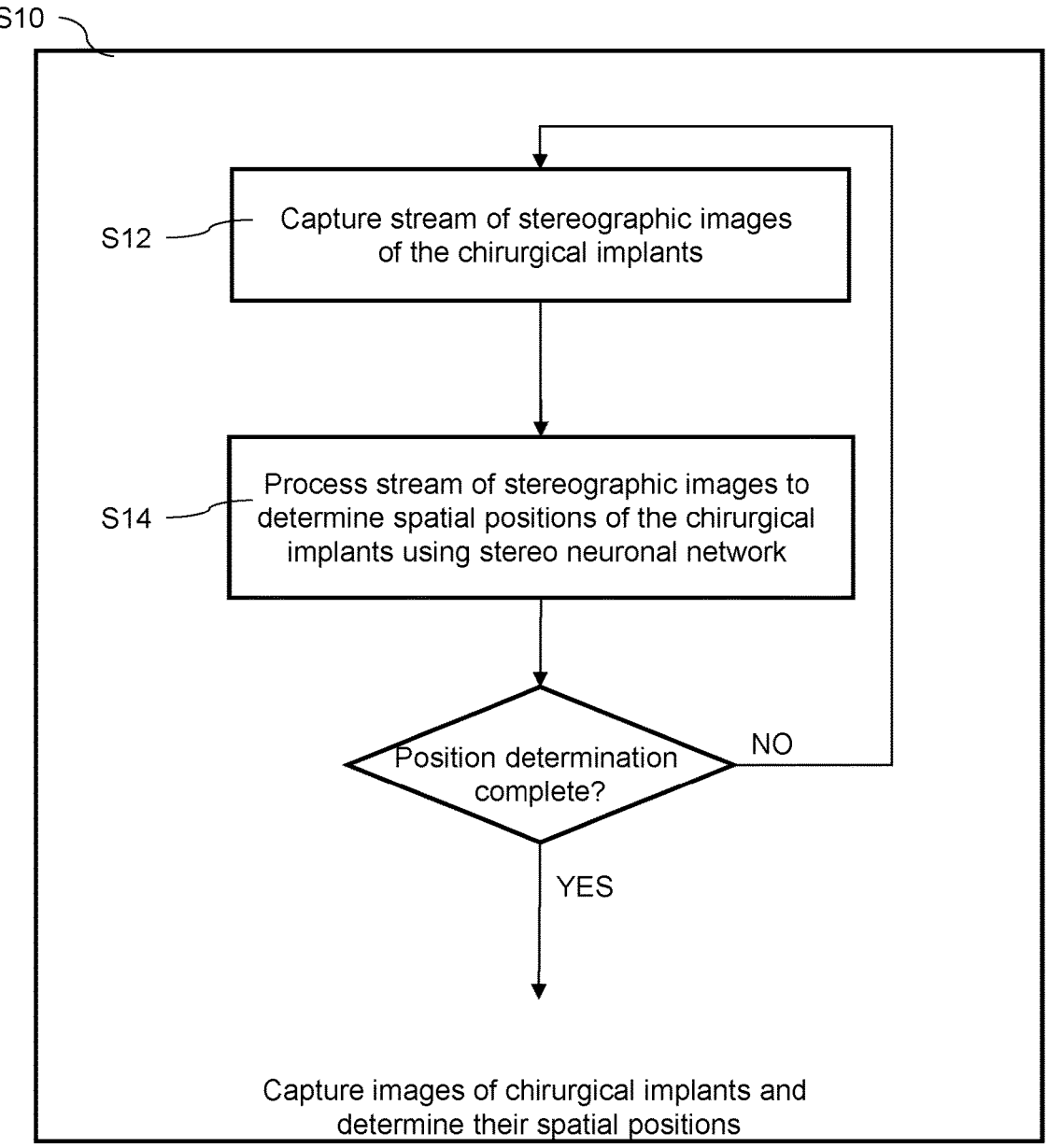
FIG. 3 shows a flowchart illustrating steps of an embodiment of determining the spatial positions of the chirurgical implants.

FIG. 3 shows the steps of determining the spatial positions of the chirurgical implants $20_{1-n}$. In substep S12, stereo images are continuously streamed from two front-facing environmental cameras 54L, 54R of a head-mounted augmented reality headset, such as a Microsoft HoloLens.

According to particular embodiments, depth information captured by the camera-based positioning device 50 (e.g., by a LIDAR and/or a time-of-flight ToF depth sensor) is also used in determining the spatial positions of the chirurgical implants $20_{1-n}$.

In a subsequent substep S14, the stream of stereo images is processed to determine the relative positions of the chirurgical implants $20_{1-n}$. The stereo images are fed to two branches of a stereo neural network, the neural network having been trained with a dataset of stereo images of chirurgical implants and corresponding annotations indicative of spatial positions P1-$n$ of the chirurgical implants captured by the dataset of stereo images. A particular implementation of the stereo neural network is described in detail with reference to FIGS. 11, 12A and 12B.

Figure 4:
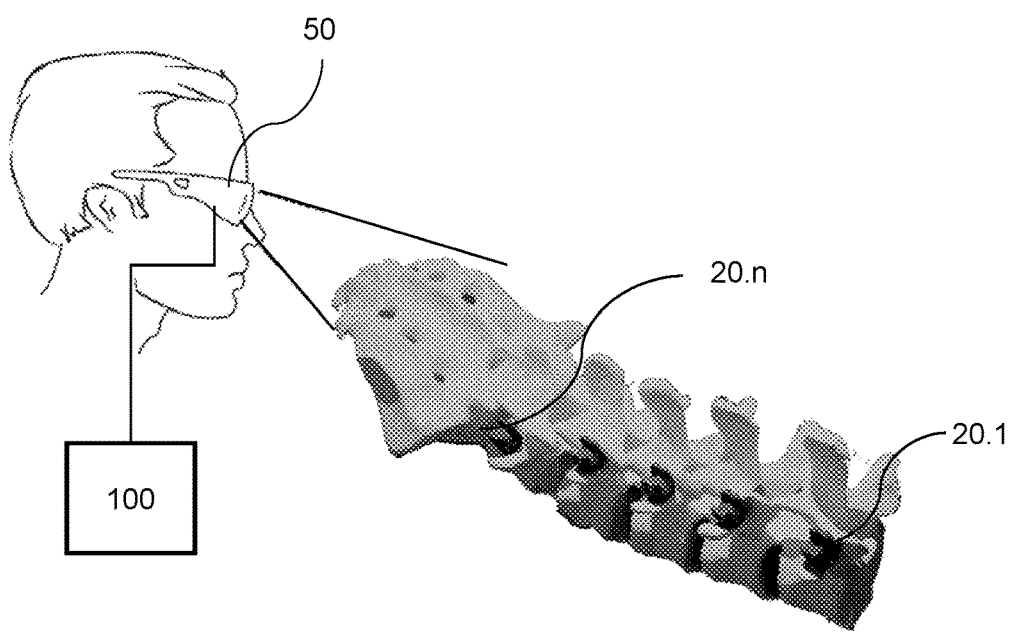
FIG. 4 shows a schematic perspective view, illustrating capturing images of a plurality of chirurgical implants implanted into a patient, using a camera-based positioning device.

FIG. 4 shows a schematic perspective view, illustrating capturing images of a plurality of chirurgical implants $20_{1-n}$ implanted into a patient, using a camera-based positioning device 50. The camera-based positioning device 50 is a head-mounted imaging and display device comprising two spaced apart image capture sensors 54L, 54R and a display device 52 for the display of overlays superimposed on a user's view therethrough. The images of the chirurgical implants $20_{1-n}$ are captured as a stream of stereo images recorded as a user, in particular a surgeon or an assistant, is positioned with a view (at least a partial) of the respective anatomical part 200 of the patient.

Figure 5:
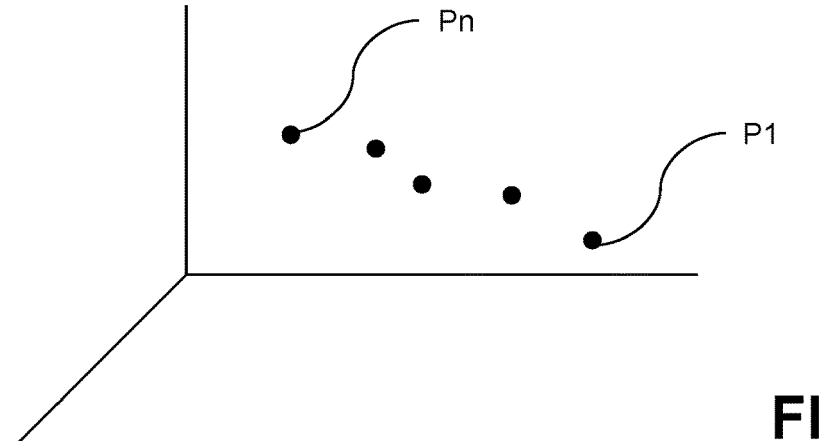
FIG. 5 shows a schematic perspective view, illustrating the spatial positions of a plurality of chirurgical implants, as determined based on the images of the plurality of chirurgical implants captured by the camera-based positioning device.

FIG. 5 shows a schematic perspective view, illustrating the spatial positions $P_{1-n}$ of a plurality of chirurgical implants $20_{1-n}$, as determined based on the stereo images of the plurality of chirurgical implants $20_{1-n}$ captured by the camera-based positioning device 50. The spatial positions $P_{1-n}$ of the chirurgical implants $20_{1-n}$ are determined in three-dimensional space using a positioning algorithm, described in detail with reference to FIGS. 11, 12A and 12B.

Figure 6:
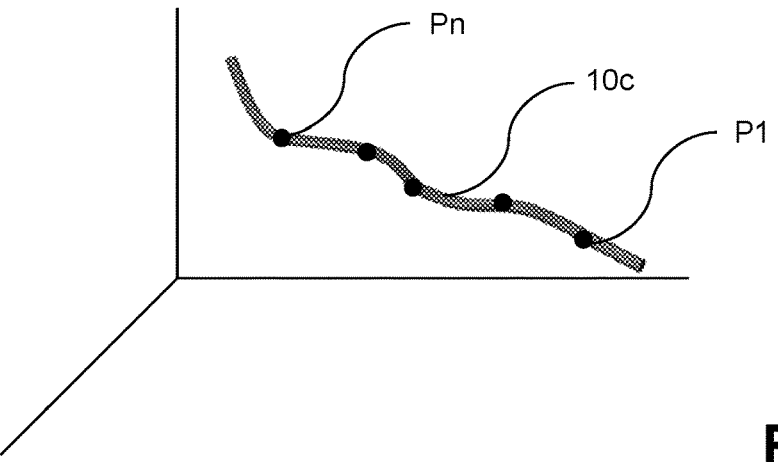
FIG. 6 shows a schematic perspective view, illustrating a calculated rod shape corresponding to the spatial positions of the plurality of chirurgical implants.

FIG. 6 shows a schematic perspective view, illustrating a calculated rod shape 10$c$ corresponding to the spatial positions $P_{1-n}$ of the plurality of chirurgical implants. The calculated rod shape 10$c$, is determined such as to allow the plurality of chirurgical implants $20_{1-n}$ to be attached to the reinforcing rod 10. Details of a particular embodiment of determining the calculated rod shape 10$c$ are described with reference to FIGS. 11, 12A and 12B, FIG. 7A illustrates the bending parameters of one of the sequence of bending parameter set(s) 1-n relative to a bending bench 70. Each bending parameter set define a series of parameters descriptive of a reinforcing rod 10 having the calculated rod shape 10c. As illustrated, the bending parameters sets each comprise a rod section distance dARP$_{1-n}$ between consecutive bends of the reinforcing rod 10; an axial reorientation angle $\alpha_{1-n}$ indicative of an angle by which the reinforcing rod needs to be rotated around its longitudinal axis between consecutive bends; and a rod bending angle $\beta_{1-n}$ indicative of an angle of a respective bend of the reinforcing rod 10 in a radial direction with respect to the reinforcing rod 10.

Details of a particular embodiment of determining the bending parameters are described with reference to FIGS. 11, 12A and 12B.

Figure 8:
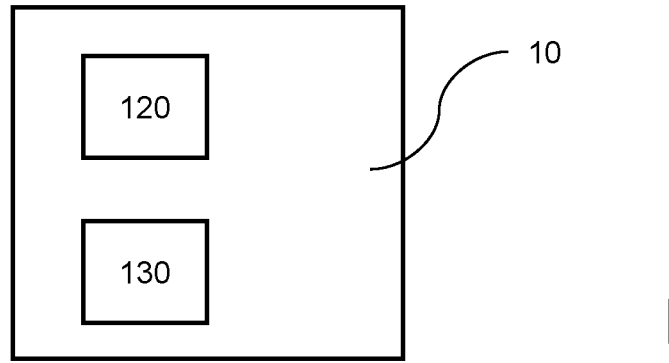
FIG. 8 shows a highly schematic block diagram of a computing device according to the present disclosure.

FIG. 8 shows a highly schematic block diagram of a computing device 100 comprising a processing unit 120 and a memory unit 130. The memory unit 130 comprises instructions, which, when executed by the processing unit 120 cause the computing device 100 to carry out the method of assisting bending of a reinforcing rod 10 according to one of the embodiments disclosed herein.

Figure 9:
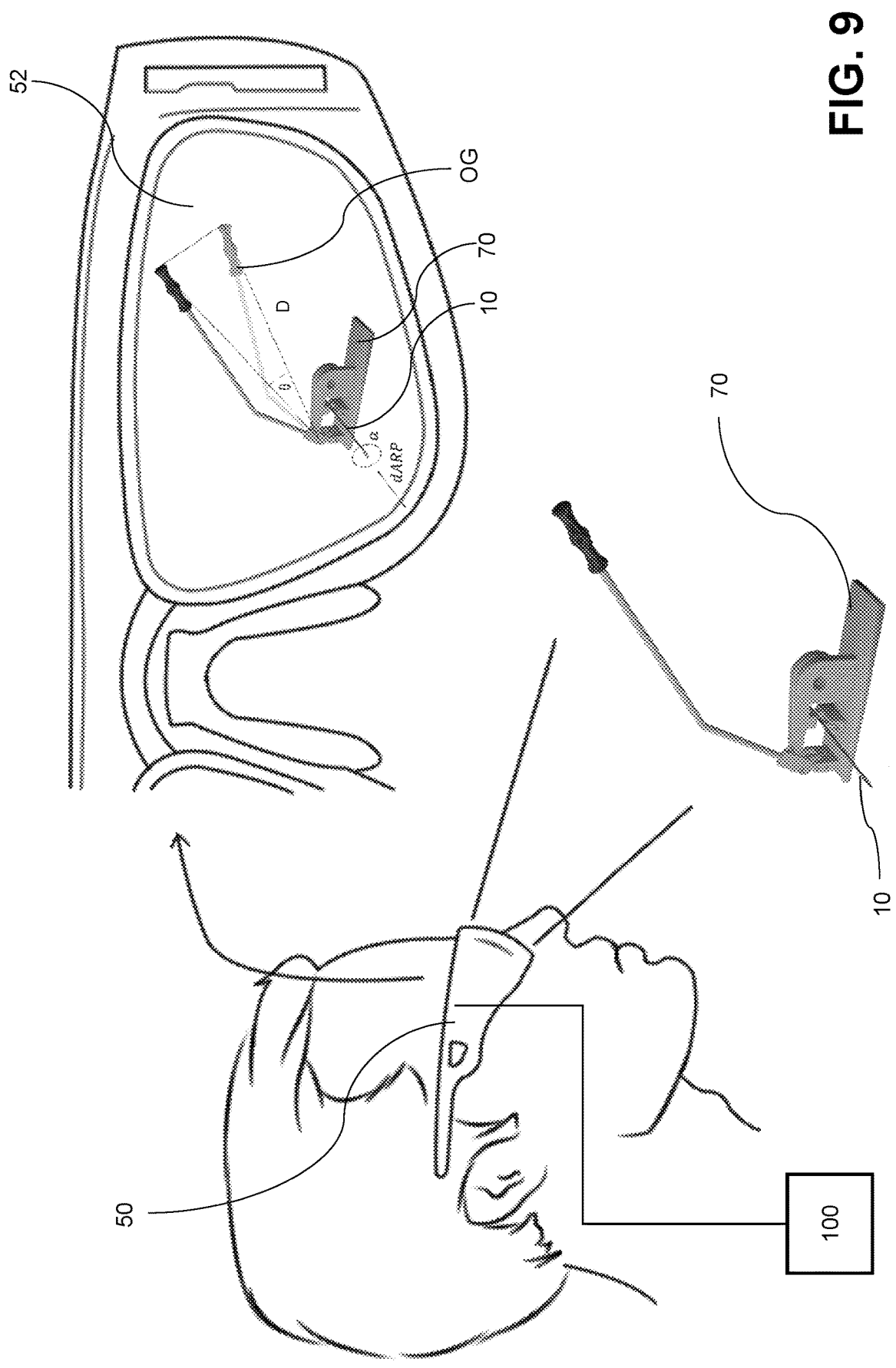
FIG. 9 shows a schematic view, illustrating display of a particular prescribed operation step of the tool operation guidance, as an overlay superimposed on a user's view of a bending tool through a see-through display of the camera-based positioning device.

FIG. 9 shows a schematic view, illustrating display of a particular prescribed operation step S$_{1-n}$ of the tool operation guidance, as an overlay OG$_{1-n}$ super-imposed on a user's view of the bending tool 70 through a see-through display 52 of the camera-based positioning device 50. As illustrated in FIG. 9, the overlay is generated as a 3D overlay OG and the camera-based positioning device 50 is controlled by the computing device 100 such that 3D overlay OG is projected in the field of view of the user, through a see-through display device 52 of a head-mounted augmented reality headset. The 3D overlay OG is projected in the field of view of the user while the user views the bending bench 70 through the display device 52, the 3D overlay OG being projected at a corresponding position with respect to the bending bench 70.

As shown, the overlay OG represents a specific operation step S$_{1-n}$ as a visualization of the bending bench 70 in an actuated position (e.g., rotational displacement of a lever arm 71) which causes the reinforcing rod 10 to be bent according to the corresponding bending parameter set.

Figure 10:
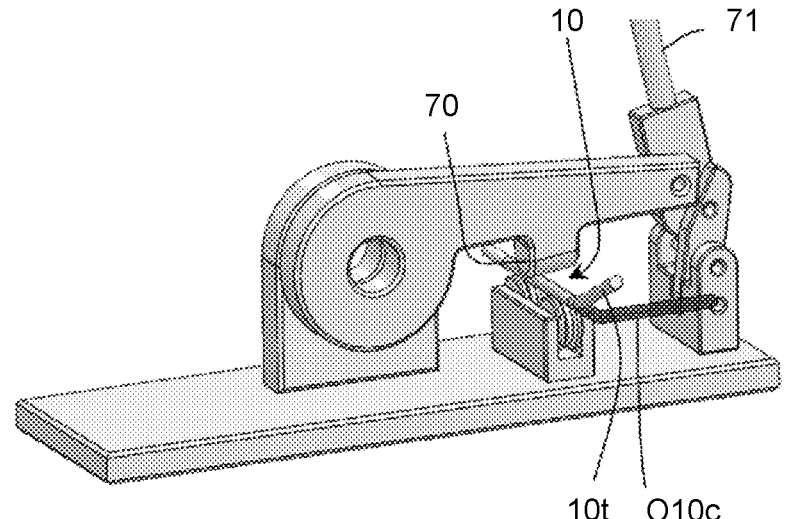
FIG. 10 shows a schematic perspective view of a bending tool receiving a reinforcing rod, illustrating superimposition of an overlay representing the calculated rod shape over a user's view of the reinforcing rod while operating a bending bench.

As illustrated on FIG. 10, in order to even further improve the user experience, respectively to allow the user to verify the progress of the sequence of prescribed operation steps S$_{1-n}$ and/or to verify the current shape of the reinforcing rod 10t, augmented reality data is generated based on the calculated rod shape 10c, comprising an overlay representing the calculated rod shape O10c as a 3D overlay. The camera-based positioning device 50 is controlled by the computing device 100 to display the overlay representing the calculated rod shape O10c on the display device 52 such that the overlay is superimposed on a user's view of the reinforcing rod 10.

Figure 11:
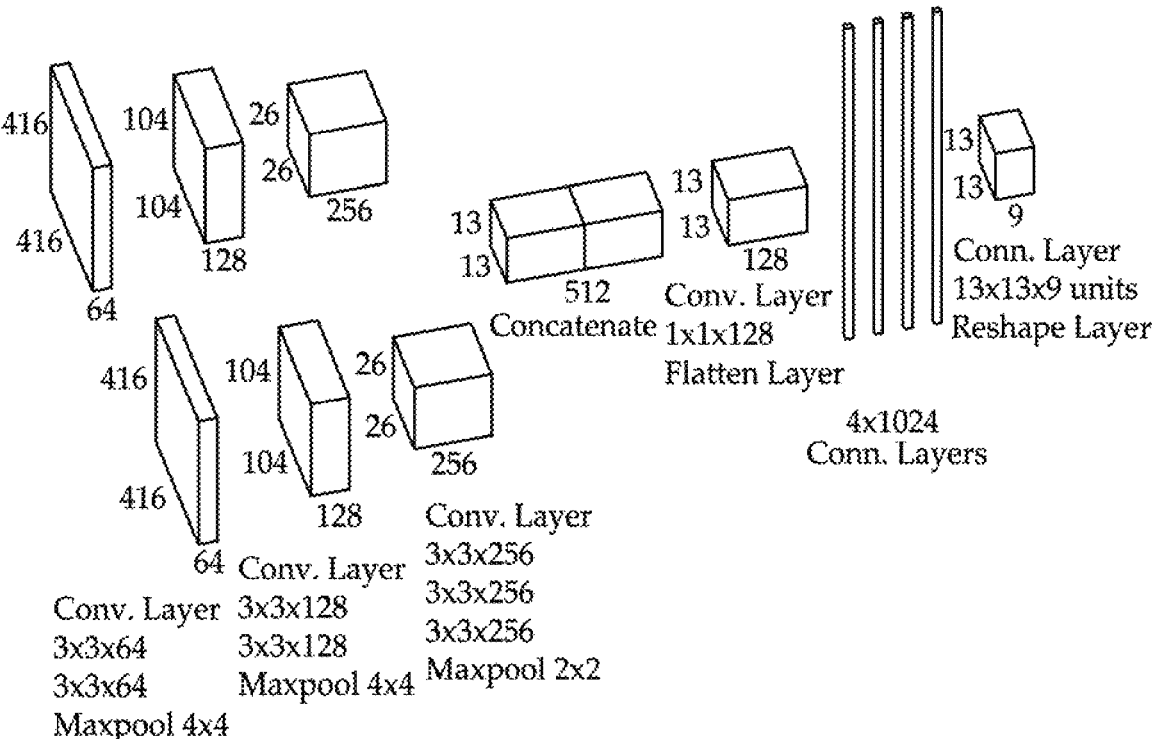
FIG. 11 shows a schematic visualization of a stereo neural network used in determining the spatial positions of the chirurgical implants.
Figure 12A:
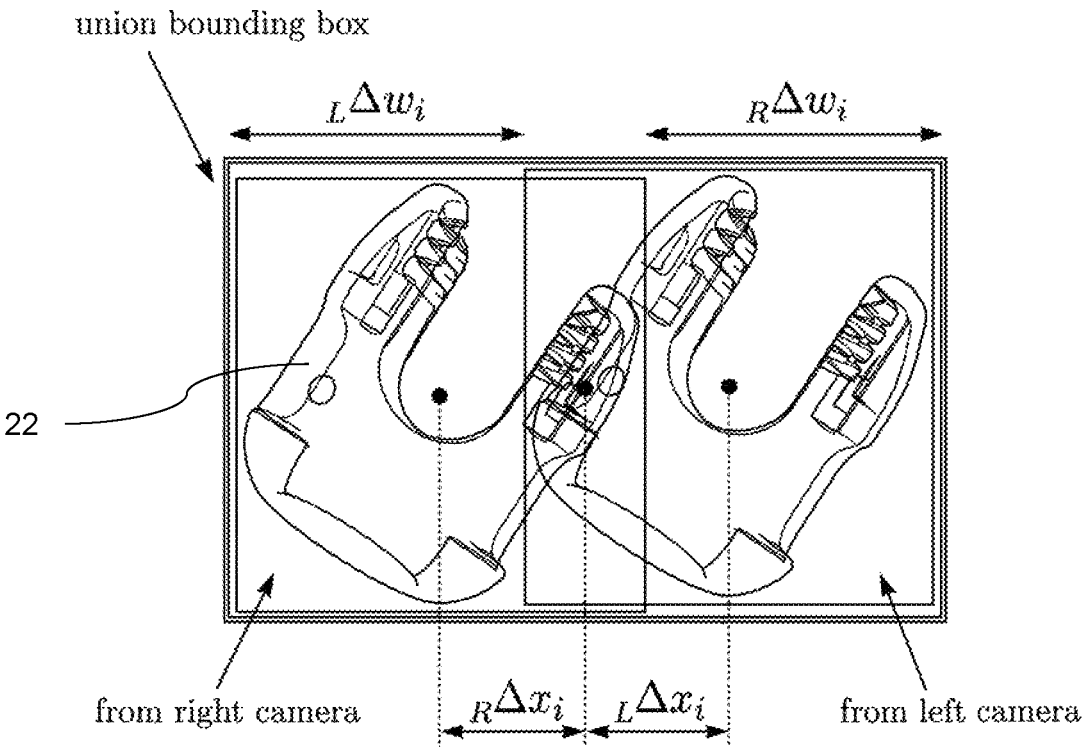
FIG. 12A shows a schematic representation of processing of stereo images to determine the spatial positions of the chirurgical implants.
Figure 12B:
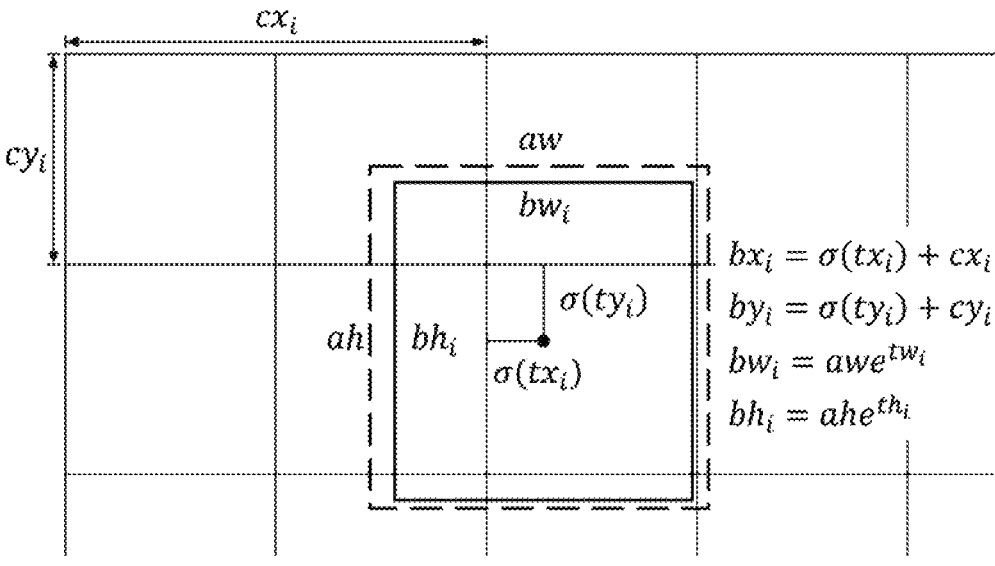
FIG. 12B shows an illustration of bounding boxes defined as part of the processing of the stereo images to determine the spatial positions of the chirurgical implants.

Turning now to FIGS. 11, 12A and 12B, a particular embodiment of determining the spatial positions of the chirurgical implants 201-n shall be described in detail. As illustrated on FIG. 11, both input branches of the neural network are configured identically. Each branch consists of three convolutional blocks composed of a series of convolutional layers with 3×3 filters which are completed by a max-pooling and a dropout layer. The activations of each convolutional layer are post-processed by a batch normalization layer. The number of filters is doubled for each convolutional block and the weights of the convolutional layers are shared by both network branches. This strategy enables the generation of consistent feature maps for the left and the right input image, respectively. In the next part of the network, the two feature maps are concatenated before a convolutional layer reduces the dimensionality of the resulting tensor using 1×1 filters. Then, four fully connected layers with 1024 units each regress the final output tensor which is brought into the desired shape by a reshape layer. The activation function for all convolutional and dense layers is a leaky Rectified Linear Unit ReLU, e.g., with a slope of 0.1 except for the last dense layer which uses linear mapping.

All bounding boxes in both stereo images are reconstructed in that the output tensor of the network is of shape 13×13×9 and contains the encoded information. According to a particular embodiment, correspondences by associating detected objects in the left and the right images are identified by superimposing the left and right input images (of the stereo images) to create a union bounding box for each pedicle screw 20$_{1-n}$ which contains both the bounding box of the left and the right image, respectively. This concept is illustrated for a single pedicle screw head 22 in FIG. 12A. The output tensor of the network can be interpreted as a 13×13 grid that divides the image into 169 cells, each consisting of nine regressed values. An output grid size of 13×13 was heuristically determined as a good trade-off that allows the detection of multiple smaller neighboring objects, such as screws, while keeping the dimensionality low. Each cell is responsible for detecting union bounding boxes whose center is located within the bounds of the cell. Each detection $\gamma i$ (i=1, ..., n, where n denotes the number of detected pedicel screws 20$_{1-n}$) and consequently each union bounding box found on each stereo image pair in the 13×13 grid is encoded by a total of nine regressed parameters organized into three groups:

$$\gamma_i = [\underbrace{ts_i}_{presence}, \underbrace{tx_i, ty_i, tw_i, th_i}_{union\ box}, \underbrace{{}_Lt\Delta x_i, {}_Lt\Delta w_i, {}_Rt\Delta x_i, {}_Rt\Delta w_i}_{stereo\ correction}]$$

The first parameter $ts_i$ indicates whether a pedicle screw 20$_{1-n}$ and consequently the center of a union bounding box is located in the respective grid cell. This parameter is a binary variable for training but needs to exceed an experimentally determined value of 0.5 to suggest screw presence during inference. The following four entries $tx_i$, $ty_i$, $tw_i$, $th_i$ define the precise location of a union bounding box as well as its width and height. In an embodiment where each cell in the 13×13 grid has unit width and height and that the top-left location of a grid cell can be described by the two values $cx_i$, $cy_i$ as depicted in FIG. 12B. Instead of regressing the union bounding box location in global pixel coordinates, all refinements are described relative to the cell location $cx_i$, $cy_i$ within the 13×13 grid, where the detection occurred. The union bounding box parameters $bx_i$, $by_i$, $bw_i$, $bh_i$ are then obtained by:

$$bx_i = \sigma(tx_i) + cx_i$$

$$by_i = \sigma(ty_i) + cy_i$$

$$bw_i = aw \cdot e^{twi}$$

$$bh_i = ah \cdot e^{thi}$$

where $\sigma$- denotes the sigmoid function. The parameters aw and ah are anchor values that introduce prior knowledge about the union bounding boxes. This prior information is obtained by averaging over manually labeled ground-truth union bounding boxes to provide an initial estimate which is corrected by the exponential terms. The anchors are of predefined size and do not depend on the current detection. The sigmoid function σ- is required to map the regressed parameters $tx_i$ and $ty_i$ into the range [0, 1] to ensure that the bounding box center will remain in the predicted grid cell.

The third group of parameters refers to the stereo correction that determines the offsets from the union bounding box to the respective bounding boxes in the left and right image. Assuming rectified cameras 54L, 54R, only the horizontal offset and the width correction for the left and right image need to be regressed (see FIG. 12A). This results in the final four parameters of the detection descriptor Lt∆xi, Lt∆wi, Rt∆xi, Rt∆wi. A prescript ● indicates from hereinafter that a term can be applied to the left and right image, respectively. The detection descriptor will be converted to absolute offsets as follows:

$$_\bullet \Delta x_i =\, _\bullet a\Delta x \cdot e^{\bullet^{t\Delta x_i}}$$

$$_\bullet \Delta w_i =\, _\bullet a\Delta w \cdot e^{\bullet^{t\Delta w_i}}$$

The parameters ●a∆x and ●a∆w are anchor values which were found by averaging over observed horizontal off-sets and width corrections in the ground-truth data, similar to the anchor values aw and ah above. With this representation, each grid cell can detect exactly one screw head 22. The bounding boxes ●($x_i$, $y_i$, $w_i$, $h_i$) in the stereo image pairs are eventually found as follows:

$$_L x_i = b x_i + {_L\Delta x_i} \quad _R x_i = b x_i - {_R\Delta x_i}$$

$$_L y_i = b y_i \quad _R y_i = b y_i$$

$$_L w_i = b w_i + {_L\Delta w_i} \quad _R w_i = b w_i - {_R\Delta w_i}$$

$$_L h_i = b h_i \quad _R h_i = b h_i$$

The final point detections in pixel-space ●(ui, vi) are found by transforming the center of the bounding boxes from the grid-space to pixel-space. This transformation consists of dividing ●(xi, yi) by 13, resulting in normalized coordinates and successive multiplication by the original image width and height, respectively.

The network according to this particular embodiment was implemented in TensorFlow and trained on a dataset obtained from ex-vivo experiments. To homogenize the dataset, all images were resized to a specific resolution and normalized. After random weight initialization, the stereo neural network was trained for 1000 epochs with a batch size of 16. The learning rate was initially set to 10-3 and was reduced to 10-4 after 750 epochs and to 10-5 for the last 100 epochs. To better generalize to unseen data, the stereo images were augmented on-the-fly for training. According to various embodiments, different augmentation strategies can be applied with varying combinations of augmentation techniques such as brightness and contrast changes, blurring, histogram equalization, scaling, vertical flipping of the image, and vertical translation. A combination of vertical translation at a probability of 50% with subsequent scaling or contrast adaptation is particularly advantageous.

Given i corresponding detections ●(ui, vi) in a stereo image pair, the 3D position of the $i^{th}$ screw candidate $\vec{csi}$ can be determined using the vector Midpoint method as follows. Let $_L\vec{n}_i$ and $_R\hat{n}_i$ be the normalized direction vectors of the rays from the respective camera center $_L\vec{c}_i$ and $_R\vec{c}_i$ to the detections $L^{(u_i, v_i)}$ and $R^{(u_i, v_i)}$. As the rays typically do not intersect, the points $_L\vec{sc}_i$ and $_R\vec{sc}_i$ on the left and the right ray which are closest to each other are determined:

$$_L\vec{sc}_i = {_L\lambda_i} \cdot {_L\vec{n}_i}$$

$$_R\vec{sc}_i = ({_R\vec{c}_i} - {_L\vec{c}_i}) + {_R\lambda_i} \cdot {_R\vec{n}_i}$$

The following equation can be stated by taking into account that to ensure shortest distance $_L\vec{sc}_i - {_R\vec{sc}_i}$, has to be perpendicular to both rays. Projecting both rays on each other and given that $_L\vec{sc}_i$ and $_R\vec{sc}_i$ coincide in this projected situation yields:

$$_L\lambda_i \cdot ({_L\vec{n}_i} \cdot {_L\vec{n}_i}) = ({_R\vec{c}_i} - {_L\vec{c}_i}) \cdot {_L\vec{n}_i} + {_R\lambda_i} \cdot ({_R\vec{n}_i} \cdot {_L\vec{n}_i})$$

$$_L\lambda_i \cdot ({_L\vec{n}_i} \cdot {_R\vec{n}_i}) = ({_R\vec{c}_i} - {_L\vec{c}_i}) \cdot {_R\vec{n}_i} + {_R\lambda_i} \cdot ({_R\vec{n}_i} \cdot {_R\vec{n}_i})$$

Solving for $_L\lambda_i$ and $_R\lambda_i$ results in:

$$_L\lambda_i = \frac{({_R\vec{c}_i} - {_L\vec{c}_i}) \cdot {_L\vec{n}_i} - ({_R\vec{c}_i} - {_L\vec{c}_i}) \cdot {_R\vec{n}_i} \cdot ({_L\vec{n}_i} \cdot {_R\vec{n}_i})}{1 - ({_L\vec{n}_i} \cdot {_R\vec{n}_i})^2}$$

$$_R\lambda_i = \frac{({_R\vec{c}_i} - {_L\vec{c}_i}) \cdot {_L\vec{n}_i} \cdot ({_L\vec{n}_i} \cdot {_R\vec{n}_i}) - ({_R\vec{c}_i} - {_L\vec{c}_i}) \cdot {_R\vec{n}_i}}{1 - ({_L\vec{n}_i} \cdot {_R\vec{n}_i})^2}$$

Finally, $\vec{sci}$ is determined by linear interpolation of $_L\vec{sc}_i$ and $_R\vec{sc}_i$ and placed in the point set of triangulated points $P_{tri}$. Each processed stereo image pair provides $N_{det}$ potential screw candidates which are expressed in a 3D world coordinate frame and stored in a point set $P_{tri}$. The goal of the subsequent clustering routine is to condense incoming screw candidate locations $\vec{sc}_i$ from $P_{tri}$ on-the-fly into a set of clustered screw positions $P_{final}$ based on the preoperatively known number of desired screws $N_{screws}$. The clustering algorithm works as follows. The first incoming screw candidate $p_{curr}$ from $P_{tri}$ is stored in a new point set P– which is added to the set of cluster candidates $P_{cand}$. Each incoming point $p_{curr}$ after that is either appended to the closest existing cluster $P_{closest} \in P_{cand}$, if the distance to the nearest cluster center is smaller than an empirically determined distance $d_{thresh}$, e.g., of 2.0 cm. Otherwise, the point $p_{curr}$ is the seed of a new point set $P_{iclu}$, which is added to $P_{cand}$. The procedure terminates as soon as $N_{screws}$ clusters are found which are supported by e.g. 100 individual points. The final clusters are determined by finding the center of each point set in $P_{cand}$ and storing it in $P_{final}$. The final estimates are presented to the surgeon for visual confirmation. In case of incorrect detections, the screw detection is restarted.

This algorithm not only reduces a potentially noisy set of screw point candidates into a distinct number of estimates, but also efficiently removes outliers due to missing support of other candidate points. Finally, Principle Component Analysis is applied to separate all points in $P_{final}$ into a point set of anatomically left points $_L P_{final}$ and right points $_R P_{final}$, respectively, and to sort all points from cranial (j=1) to caudal (j=$N_{screws}$/2).

According to particular embodiments, to allow interactive rates, some of the calculation need to be performed on a computing device such as a high-end workstation rather than onboard the camera-based positioning device 50. To this end, the stereo image data is streamed from the camera-based positioning device 50 to the computing device 100. The spatial positions of the pedicle screws 20$_{1-n}$ are calculated by the computing device 100 and are eventually sent back to the camera-based positioning device 50 for display and verification.

Once the spatial positions $P_{1-n}$ of the pedicle screws pj∈ ●Pfinal have been obtained, the tool operation guidance is generated to eventually guide surgeons.

Each bending step is characterized by a set of bending parameters, as depicted in FIG. 7A. To adjust the reinforcing rod 10 position and orientation, the chirurgical implant 20$_{1-n}$ needs to be shifted along its main axis by dARP and rotated by α. The bending angle of the reinforcing rod β is proportional to the angular displacement of the lever of the bending bench 70.

The pedicle screw head tulips 22, where the reinforcing rod 10 will eventually be mounted, has an opening that is only marginally (e.g. 0.1 mm) wider than the diameter of the reinforcing rod 10 to guarantee a strong rigid postoperative connection. This implies that the reinforcing rod 10 has to be straight in the positions where it will be mounted into the pedicle screw heads 22. To ensure straight rod segments between the screw heads 22, each screw head 22 pj in ●Pfinal is replaced by two equidistant control points and added to the respective set of control points ●$P_{control}$.

$$\bullet \mathcal{P}_{control} \leftarrow \vec{p}_j \pm \mu \cdot \frac{(\vec{p}_{j+1} - \vec{p}_{j-1})}{\|(\vec{p}_{j+1} - \vec{p}_{j-1})\|} \forall \; p_j; j = 2, \ldots, |\bullet \mathcal{P}_{final}| - 1$$

where μ is a heuristically determined parameter, e.g., set to 7.5 mm.

From this set of control points, all bending parameters can be calculated for each bending step $S_{1-n}$. The $k^{th}$ bend is characterized by the required bending angle of the reinforcing rod $\beta_k$, the axial reorientation angle αk and the distance by which the reinforcing rod 10 needs to be advanced $dARP_k$ as illustrated in FIG. 7A. Each bending angle $\beta_k$ is found by iterating over ●$P_{control}$ to determine the angles using the dot product:

$$\beta_k = \arccos\left(\frac{p_{k+1} - p_k}{\|p_{k+1} - p_k\|} \cdot \frac{p_{k-1} - p_k}{\|p_{k-1} - p_k\|}\right) \forall \; p_k; k = 2, \ldots, |\bullet \mathcal{P}_{control}| - 1$$

The axial reorientation angle αk for the $k^{th}$ bend is calculated by taking four control points into account and initially generating the following three vectors:

$$\left. \begin{array}{ll} _L\vec{n}_k & = \frac{p_{k-1} - p_k}{\|p_{k-1} - p_k\|} \\ _C\vec{n}_k & = \frac{p_{k+1} - p_k}{\|p_{k+1} - p_k\|} \\ _R\vec{n}_k & = \frac{p_{k+2} - p_{k+1}}{\|p_{k+2} - p_{k+1}\|} \end{array} \right\} \forall \; p_k; k = 2, \ldots, |\bullet \mathcal{P}_{control}| - 2$$

In a next step, the vectors $_L\vec{n}_k$ and $_R\vec{n}_k$ are projected on the plane defined by the normal vector $_C\vec{n}_k$ resulting in the projected $_L\tilde{n}_k$ and $_R\tilde{n}_k$. Lastly, the axial reorientation angle for the $k^{th}$ bending step is found by:

$$\alpha_k = \arccos(_L\tilde{n}_k \cdot _R\tilde{n}_k)$$

The distance $dARP_k$ that the reinforcing rod 10 needs to be displaced in the $k_{th}$ bending step $S_k$ is determined by the Euclidean distance between the last and the current control point.

The lever angle $\theta_k$ of the bending bench 70 depends on the desired rod bending angle $\beta_k$. Any bending can be considered a combination of elastic and plastic deformation of the reinforcing rod 10. Small lever angles result in no permanent rod 10 deformation due to elastic deformation. The relationship between any desired rod angle β and any applied lever angle θ, however, can be approximated to be linear as soon as plastic deformation starts to occur. This results in a transfer function of the form β=f(θ)=mθ+t, where β is the desired bending angle of the reinforcing rod, θ corresponds to the difference in lever angle from start to end position of the bend and m and t denote the slope and offset of the linear model, respectively. Since the end of the lever 71 describes a circular movement with respect to the center of rotation, the relationship between the straight distance traveled by the tip of the lever dLever and the resulting difference in lever angle θ is given by the equation of a chord which is $$dLever = 2 \cdot r \cdot \sin\frac{\theta}{2},$$

Where r denotes the straight line distance from lever base to lever tip as depicted in FIG. 7A. The respective resulting bending angles of the reinforcing rod β may be determined from a CT scan to estimate the aforementioned linear transfer function in a least square sense.

It is claimed:

1. A computer implemented method of assisting bending of a reinforcing rod (10), the method comprising the steps carried out by a computing device (100):

a. receiving spatial positions ($P_{1-n}$) of a plurality of chirurgical implants (20$_{1-n}$) captured by a camera-based positioning device (50);

b. calculating a rod shape (10$c$) corresponding to the spatial positions ($P_{1-n}$) of the plurality of chirurgical implants (20$_{1-n}$), allowing the plurality of chirurgical implants (20$_{1-n}$) to be attached to the reinforcing rod (10);

c. based on the calculated rod shape (10$c$), calculating a sequence of bending parameter set(s);

d. generating tool operation guidance for bending tool(s) (70) based on the bending parameter set(s), the tool operation guidance indicating a sequence of prescribed operation steps ($S_{1-n}$) of the bending tool(s) (70), wherein the sequence of prescribed operation steps ($S_{1-n}$) are determined such, that when carried out using the bending tool(s) (70), causes the bending tool(s) (70) to shape the reinforcing rod (10) from an initial shape (10$i$) to a shaped form (10$s$) corresponding to the calculated rod shape (10$c$); and e. generating augmented reality data based on the tool operation guidance, the augmented reality data comprising overlay(s) representing one or more of the prescribed operation steps ($S_{1-n}$) of the tool operation guidance ($OG_{1-n}$) for superimposing on a user's view of the bending tool(s) (70), the overlay(s) comprising visualization(s) of the bending tool(s) (70) in actuated position(s) which actuated position(s) cause the reinforcing rod (10) to be bent according to the bending parameter set(s).

2. The method according to claim 1, further comprising controlling the camera-based positioning device (50) to display the overlay(s) representing the tool operation guidance ($OG_{1-n}$) on a display device (52) comprising a see-through display device (52) of the camera-based positioning device (50), the overlay(s) ($OG_{1-n}$) being superimposed on a user's view of the bending tool(s) (70) through the display device (52) and/or on the display device (52).

3. The method according to claim 1, further comprising:
a. controlling the camera-based positioning device (50) to track a progress of a user's operation of the bending tool(s) (70) in accordance with the sequence of prescribed operation steps ($S_{1-n}$) of the bending tool(s) (70); and
b. controlling the display device (52) to display the overlay ($OG_{1-n}$) representing a particular operation step (Sx) of the sequence of prescribed operation steps ($S_{1-n}$) of the tool operation guidance ($OG_{1-n}$) according to the tracking.

4. The method according to claim 1, further comprising generating augmented reality data based on the calculated rod shape (10c), the augmented reality data comprising an overlay representing the calculated rod shape (O10c).

5. The method according to claim 4, further comprising controlling the camera-based positioning device (50) such as to display the overlay representing the calculated rod shape (O10c), on a display device (52) comprising a see-through display device (52) of the camera-based positioning device (50), the overlay representing the calculated rod shape (O10c) being superimposed on a user's view of the reinforcing rod (10) through the display device (52) and/or on the display device (52).

6. The method according to claim 1, wherein the tool operation guidance is generated based on at least one of:
i. parameter(s) of the bending tool(s) (70);
ii. parameter(s) of the reinforcing rod (10); and
iii. the positions of fixation points (22) of the plurality of chirurgical implants ($20_{1-n}$).

7. The method according to claim 1, further comprising:
a. controlling the camera-based positioning device (50) to capture image(s) of the plurality of chirurgical implants ($20_{1-n}$); and
b. determining the positions of the plurality of chirurgical implants ($20_{1-n}$) based on the captured images.

8. The method according to claim 7, wherein the computing device controls the camera-based positioning device (50) to capture stereo images of the plurality of chirurgical implants ($20_{1-n}$) using image capture sensors (54L, 54R) of the camera-based positioning device (50), and wherein the computing device determines the spatial positions ($P_{1-n}$) of the plurality of chirurgical implants ($20_{1-n}$) by processing the stereo images.

9. The method according to claim 8, further comprising:
a. controlling the camera-based positioning device (50) to capture a stream of stereo images of the plurality of chirurgical implants ($20_{1-n}$); and
b. iteratively refining the determined spatial positions ($P_{1-n}$) of the plurality of chirurgical implants ($20_{1-n}$) by processing the stream of stereo images.

10. The method according to claim 8, wherein the computing device determines the spatial positions ($P_{1-n}$) of the plurality of chirurgical implants ($20_{1-n}$) by processing the stereo images using a stereo neural network, the neural network having been trained with a dataset of stereo images of chirurgical implants and corresponding annotations indicative of spatial positions of chirurgical implants.

11. The method according to claim 1, wherein a bending parameter set(s) comprises at least one of:
i. a rod distance ($dARP_{1-n}$);
ii. an axial reorientation angle ($\alpha_{1-n}$);
iii. a rod bending angle ($\theta_{1-n}$); and
iv. a bending radius ($R_{1-n}$).

12. The method according to claim 1, further comprising:
a. controlling the camera-based positioning device (50) to capture image(s) of the bending tool(s) (70); and
i. identifying the bending tools(s) (70) using the captured images and retrieve parameter(s) of the bending tool(s) (70) based on the identification; or
ii. determining parameter(s) of the bending tool(s) (70) using the captured images.

13. A computing device (100) comprising a processing unit (120) and a memory unit (130) comprising instructions, which, when executed by the processing unit (120) cause the computing device (100) to carry out the method according to claim 1.

14. A system (1) for assisting bending of a reinforcing rod (10), the system (1) comprising:
a. a computing device (100) according to claim 12; and
b. a camera-based positioning device (50) communicatively connected to the computing device (100), the camera-based positioning device (50) comprising two or more image capture sensors (54L, 54R) and a display device (52) for the display of overlay(s) superimposed on a user's view.

15. A computer program product, comprising instructions, which, when carried out by a processing unit (120) of a computing device (100), cause the computing device (100) to carry out the method according to claim 1.

16. The method of claim 1 wherein the plurality of chirurgical implants ($20_{1-n}$) comprise pedicle screws.

\* \* \* \* \*